US011154471B2

(12) United States Patent
Thomas et al.

(10) Patent No.: US 11,154,471 B2
(45) Date of Patent: *Oct. 26, 2021

(54) FLEXIBLE SOLID COSMETIC COMPOSITION COMPRISING SULFONATE ANIONIC SURFACTANTS, FATTY ESTERS AND FATTY ALCOHOLS, AND COSMETIC TREATMENT METHOD

(71) Applicant: L'OREAL, Paris (FR)

(72) Inventors: Béatrice Thomas, Saint-Ouen (FR); Frederik Pinay, Saint-Ouen (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/466,774

(22) PCT Filed: Nov. 21, 2017

(86) PCT No.: PCT/EP2017/079942
§ 371 (c)(1),
(2) Date: Jun. 5, 2019

(87) PCT Pub. No.: WO2018/104048
PCT Pub. Date: Jun. 14, 2018

(65) Prior Publication Data
US 2019/0380932 A1 Dec. 19, 2019

(30) Foreign Application Priority Data

Dec. 9, 2016 (FR) .................................. FR1662217

(51) Int. Cl.
A61K 8/34 (2006.01)
A61K 8/02 (2006.01)
A61K 8/37 (2006.01)
A61K 8/46 (2006.01)
A61Q 5/12 (2006.01)
A61Q 19/10 (2006.01)

(52) U.S. Cl.
CPC ............ A61K 8/342 (2013.01); A61K 8/0216 (2013.01); A61K 8/375 (2013.01); A61K 8/466 (2013.01); A61Q 5/12 (2013.01); A61Q 19/10 (2013.01)

(58) Field of Classification Search
None
See application file for complete search history.

(56) References Cited

U.S. PATENT DOCUMENTS

| 3,472,840 A | 10/1969 | Stone et al. |
| 3,589,978 A | 6/1971 | Kamal et al. |
| 3,910,862 A | 10/1975 | Barabas et al. |
| 4,031,307 A | 6/1977 | DeMartino et al. |
| 4,165,367 A | 8/1979 | Chakrabarti |
| 10,548,832 B2 * | 2/2020 | Thomas ................. A61K 8/463 |
| 10,555,890 B2 * | 2/2020 | Thomas ............... A61K 8/8158 |
| 2014/0314697 A1 | 10/2014 | Wang et al. |
| 2015/0352027 A1 | 12/2015 | Thomas et al. |

FOREIGN PATENT DOCUMENTS

| FR | 1492597 A | 8/1967 |
| FR | 2077143 A5 | 10/1971 |
| FR | 2393573 A1 | 1/1979 |
| WO | 2014/111655 A2 | 7/2014 |

OTHER PUBLICATIONS

International Search Report and Written Opinion for Application No. PCT/EP2017/079942, dated Dec. 22, 2017.
Mintel: "Red-Yellow-Green Elastic Soap," DM Drogerie Market, XP002769826, Feb. 2015.
Mintel: "Shampaste Shampoo," Sebastian, XP002769825, Oct. 1999.
Mintel: "Ultra Rich Soap-Free Cleansing Bar," Laboratoires Dermatologiques Avene, XP002769827, Nov. 2007.
Todd, Charles, et al., "Volatile Silicone Fluids for Cosmetic Formulations," Cosmetics and Toiletries, vol. 91, Jan. 1976, pp. 29-32.

* cited by examiner

Primary Examiner — Katherine Peebles
(74) Attorney, Agent, or Firm — The Marbury Law Group, PLLC

(57) ABSTRACT

Flexible solid cosmetic composition comprising sulfonate anionic surfactants, fatty esters and fatty alcohols, and cosmetic treatment method The present invention relates to an aqueous cosmetic composition in flexible solid form, comprising (i) at least 10% by weight of anionic surfactants comprising a sulfonate group, (ii) esters of fatty acid(s) comprising at least 12 carbon atoms, and (iii) fatty alcohols comprising at least 16 carbon atoms. The composition finds a particular application as a composition for cleaning or washing keratin materials, in particular the hair. The invention also relates to a cosmetic treatment method, in particular for caring for, cleaning and/or conditioning keratin materials using said composition.

20 Claims, No Drawings

FLEXIBLE SOLID COSMETIC COMPOSITION COMPRISING SULFONATE ANIONIC SURFACTANTS, FATTY ESTERS AND FATTY ALCOHOLS, AND COSMETIC TREATMENT METHOD

CROSS REFERENCE TO RELATED APPLICATION

This is a national stage application of PCT/EP2017/079942, filed internationally on Nov. 21, 2017, which claims priority to French Application No. 1662217, filed on Dec. 9, 2016, both of which are incorporated by reference herein in their entireties.

The present invention relates to cosmetic compositions, in particular for cleaning or washing keratin materials, in particular the hair, which are in flexible solid form, and also to a cosmetic treatment method using same.

Many cosmetic washing products are known in the hair hygiene field. They are generally intended for cleaning keratin materials while at the same time providing them with good cosmetic properties (conditioning, hydration, softness, sheen, etc). Conventional products for cleaning keratin materials, such as shampoos, are usually in the form of liquids or creams which are more or less viscous.

However, these products are generally difficult to meter out: the more liquid they are, the greater their tendency to run through the fingers, making it difficult to meter them out and creating waste, and/or the greater their tendency to leak out of their packaging, which can be very bothersome when they come into contact with clothing, for example during moving.

In order to modify the texture, and in particular to make it more compact, conventional means consist in using thickeners, but this is often done to the detriment of the cosmetic effects of the composition. In addition, it has been noted that thicker compositions often have the drawback of requiring a lot of rinsing water in order to remove the surplus product on the hair. In many countries where access to water is restricted, the rinsing time and therefore the amount required to properly rinse off the product are key indicators of the use qualities of a composition.

In order to overcome some of these problems, solid cosmetic formulations have been provided, but they generally have the drawback of being difficult to fractionate and/or to disintegrate on contact with water, making their use difficult and also requiring quite a large amount of water for optimum use. Moreover, the rapidity of the initiation of foaming is not optimal with these thick or solid compositions. Finally, these products do not always leave a clean natural feel to keratin materials, after removal with water. In addition, users increasingly seek new textures and new concepts for products for washing keratin materials.

Compositions for washing keratin materials which do not run, and which are more compact, modellable and economical, have therefore been proposed, for example by WO 2014/111655; they are easy to apply while at the same time enabling rapid foam initiation, in an abundant amount. These compositions are in flexible solid form, and comprise at least 12% by weight of one or more sulfonic anionic surfactants and also polymeric or non-polymeric conditioning agents. In one particular embodiment, these compositions can also comprise fatty substances, in particular fatty esters such as solid fatty diesters, for instance glycol distearate, which also has the ability to confer pearlescent properties on the compositions.

It has been noted that some of these compositions in flexible solid form and comprising surfactants comprising a sulfonate group can exhibit stability problems when they are stored. In particular, these compositions can exhibit phase separation, in particular after prolonged storage at 45° C.

It has thus been noted that the viscosity of the compositions and/or their hardness can change over time: they increase and lead to hardening of the product, which might generate difficulties in using them, in particular in sampling and applying the composition. These drawbacks can be all the more marked when these compositions undergo temperature increase and decrease cycles, which can occur during prolonged storage.

Without being bound by the present explanation, it may be considered that, during storage, the system comprising sulfonate surfactants modifies, in particular in the presence of solid fatty substances, at ambient temperature: it may destructure and then restructure differently, that is to say recrystallize in a different form, in particular during the various temperature increase and decrease cycles.

The objective of the present invention is to provide a composition in flexible solid form, which exhibits improved stability over time, in particular a viscosity and/or a hardness that is (are) constant over time.

A subject of the present invention is an aqueous cosmetic composition in flexible solid form, comprising:
  (i) at least 10% by weight of one or more anionic surfactants comprising a sulfonate group,
  (ii) one or more esters of fatty acid(s) comprising at least 12 carbon atoms, and
  (iii) one or more fatty alcohols comprising at least 16 carbon atoms,
with a (ii)/(iii) weight ratio between the ester(s) of fatty acid(s) comprising at least 12 carbon atoms (ii) and the fatty alcohol(s) comprising at least 16 carbon atoms (iii) of between 0.5 and 5.

The composition according to the invention has an entirely unusual texture, which is non-tacky and relatively firm; it is simple to take, to handle and to apply; the composition is easy to grasp and does not run between the fingers. It can be very easily metered out and applied; it does not run and rinses off easily, while giving the keratin materials a natural and clean feel after removal.

In addition, the combination according to the invention makes it possible to obtain a flexible solid texture variety, without the addition of thickener; the distribution of the composition on the keratin materials is improved, and the rapidity of initiation of foaming and the rinsing time are also improved.

Finally, the composition according to the invention is stable over time, its viscosity does not vary during storage, for example at 45° C. for 2 months. No occurrence of phase separation is observed, nor is any strong increase in the hardness of the product. Consequently, the usage qualities of the composition are not impacted. It makes it possible to obtain an abundant foam, which rinses off easily and rapidly; the composition imparts good cosmetic properties on the hair, in particular sensitized hair.

In addition, the composition according to the invention exhibits an improved flexibility, that is to say that the composition can be easily grasped (can be easily taken). Indeed, a composition with a texture that is not very (or not sufficiently) flexible (harder) will pose a problem during its use: it will be difficult for the consumer to take just the right amount required for the expected effect, to distribute the composition on the keratin materials and to have good foam initiation. This flexibility is, moreover, preserved over time.

Finally, it has been noted that, with the invention, it is possible to obtain a composition that is sufficiently flexible to be easily grasped without requiring expansion of the product; this thus makes it possible to avoid any expansion step and the process for producing the composition is thus thereby facilitated.

Preferentially, the composition according to the invention is non-colouring.

According to the present invention, the term "non-colouring composition" is intended to mean a composition not containing any dye for keratin fibres such as direct dyes or oxidation dye precursors (bases and couplers). If they are present, their content does not exceed 0.005% by weight, relative to the total weight of the composition. Specifically, at such a content, only the composition would be dyed, i.e. no dyeing effect would be observed on the keratin fibres.

Advantageously, the composition according to the invention is a foaming composition.

The composition according to the invention is therefore in flexible solid form.

The term "flexible solid" is intended to mean in particular the fact that the composition does not flow under its own weight, but it can be deformed by pressure, for example with a finger; its consistency is similar to that of a butter (without the fatty nature of course), malleable and graspable. The composition can be easily modelled in the hand; it can also be easily broken in the hand in order to take only the required amount of product. In particular, this composition can be packaged in single-dose form, for example in the form of sachets.

Preferably, the flexible solid composition according to the invention meets at least one of the physicochemical criteria hereinafter, in particular at least two criteria, preferentially the three criteria.

Preferably, the flexible solid composition according to the invention meets at least criterion 3, that is say that, advantageously, it has a penetration force as defined below.

Unless otherwise indicated, these criteria are measured at ambient temperature (25° C.) and atmospheric pressure (1 atm), the composition having undergone centrifugation for 15 minutes at 10 kg in order to remove the bubbles for the evaluation of criteria 1 and 2.

Criterion 1:

the composition according to the invention has a viscoelastic spectrum at 25° C., measured between $10^{-2}$ Hz and 100 Hz, such that there is no crossover point between the curves G' and G'', G' always being strictly greater than G'' (for measurements carried out at a frequency of between $10^{-2}$ Hz and 100 Hz).

The viscoelastic spectrum is established using a Thermo Haake RS600 imposed-stress rheometer in cone-plate geometry. The temperature was regulated by a Peltier-effect plane and an anti-evaporation device (solvent trap filled with water for the measurements at 25° C.).

Measurements were carried out with oscillation between $10^{-2}$ Hz and 100 Hz, at a strain of 0.03% with a sanded C60 1°/Ti cone and/or at a strain of 0.05% with a sanded C35 2/Ti cone.

G', which corresponds to the storage modulus reflecting the elastic response and the solid nature of the sample, is measured; G'', which corresponds to the loss modulus reflecting the viscous response and the liquid nature of the sample, is also measured.

Criterion 2:

the composition according to the invention is such that it has a threshold stress at 25° C. greater than or equal to 100 Pa.

The threshold stress is determined by scanning under stress at 25° C. An imposed-stress Thermo Haake RS600 rheometer with sanded cone-plate geometry is used. The temperature was regulated by a Peltier-effect plane and an anti-evaporation device (solvent trap filled with water for the measurements at 25° C.).

A logarithmic stress ramp from 0.1 to 250 Pa is performed over a period of 2 minutes. Two adjustment lines corresponding to the stationary regimes (solid and liquid behaviours) are plotted on the curve representing the strain as a function of the stress (logarithmic coordinates). The intersection of these two lines gives the value sought. The composition according to the invention is such that it has a threshold stress greater than or equal to 100 Pa, preferably ranging from 100 to 900 Pa, at 25° C.

Criterion 3:

the composition according to the invention is such that it has a penetration force at 25° C. greater than or equal to 40 g.

The penetration force is determined by penetrometry, with a tip having a diameter of 1.5 cm and at a speed of 10 mm/s. The texture analysis measurements are carried out at 25° C. using a Stable Micro Systems TA.XT Plus texture analyser. The penetrometry experiments are carried out with a metal rod which has a Delrin screw tip, 15 mm in diameter and 6 mm high, connected to the measuring head. The piston pushes into the sample at a constant speed of 10 mm/s, to a height of 15 mm or 20 mm depending on the height of product in the pot (of diameter 90 mm, and height 30 mm, made of plastic). The force exerted on the piston is recorded and the average value of the force is calculated.

The composition according to the invention is such that it has a penetration force at 25° C. greater than or equal to 40 g, preferably ranging from 40 to 900 g, better still ranging from 50 to 800 g, in particular ranging from 50 to 700 g, or even from 50 to 600 g.

Preferably, the composition according to the invention is such that it has a penetration force at 25° C. greater than or equal to 40 g, preferably ranging from 40 to 900 g, better still ranging from 50 to 800 g.

Better still, the composition according to the invention is such that it has both a threshold stress at 25° C. greater than or equal to 100 Pa, preferably ranging from 100 to 900 Pa; and a penetration force at 25° C. greater than or equal to 40 g, preferably ranging from 40 to 900 g, better still ranging from 50 to 800 g.

In the present description, the expression "at least one" is equivalent to the expression "one or more", and the expression "between . . . and . . . " is equivalent to the expression "ranging from . . . to . . . ", which implies that the limits are included.

(i) Anionic Surfactants

The composition according to the invention comprises at least 10% by weight of one or more anionic surfactants comprising a sulfonate group ($OSO_3H$, $OSO_3^-$).

A mixture of anionic surfactants may of course be used.

The sulfonate anionic surfactants according to the invention can optionally also comprise one or more carboxylate and/or sulfate groups; they can also be oxyalkylenated, in particular oxyethylenated, and then preferably comprise from 1 to 50 ethylene oxide units and better still from 2 to 10 ethylene oxide units.

The sulfonate anionic surfactants that can be used, comprising at least one sulfonate function ($-SO_3H$ or $-SO_3^-$, can be chosen from the following compounds: alkyl sulfonates, alkylamidesulfonates, alkylarylsulfonates, alpha-olefin sulfonates, paraffin sulfonates, alkylsulfosuccinates, alkyl ether sulfosuccinates, alkylamidesulfosuccinates, alkylsulfoacetates, N-acyltaurates, acyl isethionates; alkylsulfolaurates; and also the salts of these compounds; the alkyl groups of these compounds comprising from 6 to 30 carbon atoms, in particular from 12 to 28, better still from 14 to 24 or even from 16 to 22 carbon atoms; the aryl group preferably denoting a phenyl or benzyl group;

these compounds possibly being polyoxyalkylenated, in particular polyoxyethylenated, and then preferably comprising from 1 to 50 ethylene oxide units and better still from 2 to 10 ethylene oxide units.

In general, when the anionic surfactant is in salt form, said salt may be chosen from alkali metal salts, such as the sodium or potassium salt, ammonium salts, amine salts and in particular amino alcohol salts, and alkaline-earth metal salts, such as the magnesium salt.

Examples of amino alcohol salts that may be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts are preferably used.

Preferentially, the sulfonate anionic surfactants are chosen, alone or as a mixture, from:
  $C_6$-$C_{24}$ and in particular $C_{12}$-$C_{20}$ alkylsulfosuccinates, in particular laurylsulfosuccinates;
  $C_6$-$C_{24}$ and in particular $C_{12}$-$C_{20}$ alkyl ether sulfosuccinates;
  ($C_6$-$C_{24}$)acyl isethionates and preferably ($C_{12}$-$C_{18}$)acyl isethionates;
in particular in the form of alkali metal or alkaline-earth metal, ammonium or amino alcohol salts.

Most particularly, the anionic surfactants comprising a sulfonate group are chosen from acyl isethionates having an acyl group comprising from 6 to 30 carbon atoms, better still from 12 to 24, even better still from 16 to 22 carbon atoms.

They preferably correspond to the following formula (A): R—C(O)—O—$CH_2CH_2SO_3M$, in which R—C(O) is an acyl group preferably comprising from 6 to 30 carbon atoms, better still from 12 to 24, even better still from 16 to 22 carbon atoms, and M denotes a cosmetically acceptable counterion.

A mixture of anionic surfactants chosen from acyl isethionates can quite obviously be used.

Preferably, the composition according to the invention comprises one or more anionic surfactants chosen from cocoyl isethionates and/or lauroyl isethionates, preferentially from cocoyl isethionates, in particular in sodium salt form.

The composition according to the invention can also comprise one or more additional anionic surfactants, different from the abovementioned surfactants comprising a sulfonate group.

The additional anionic surfactants can be chosen from anionic surfactants comprising a sulfate and/or carboxylate group and not comprising a sulfonate group; they can be oxyalkylenated and then preferably comprise from 1 to 50 ethylene oxide units, better still from 2 to 10 ethylene oxide units.

The additional anionic surfactants can in particular be chosen from alkyl sulfates, alkyl ether sulfates, acylsarcosinates and acyl glutamates, and the corresponding acid forms, the alkyl and/or acyl groups of these compounds comprising from 6 to 30 carbon atoms, better still from 12 to 24, or even from 16 to 22 carbon atoms.

The composition can comprise one or more additional anionic surfactants advantageously chosen, alone or as a mixture, from:
  $C_6$-$C_{24}$ and in particular $C_{12}$-$C_{20}$ alkyl sulfates;
  $C_6$-$C_{24}$ and in particular $C_{12}$-$C_{20}$ alkyl ether sulfates; preferably comprising from 2 to 20 ethylene oxide units;
  $C_6$-$C_{24}$ and in particular $C_{12}$-$C_{20}$ acyl glutamates; in particular stearoylglutamates;
  $C_6$-$C_{24}$ and in particular $C_{12}$-$C_{20}$ acylsarcosinates; in particular palmitoylsarcosinates;
and also the salts thereof, in particular the alkali metal or alkaline-earth metal salts and in particular the sodium or magnesium salts.

The total amount of anionic surfactant(s) comprising a sulfonate group present in the composition of the invention is at least 10% by weight relative to the weight of the composition; it preferably ranges from 10% to 70% by weight, better still from 12% to 50% by weight, even better still from 15% to 45% by weight, preferentially from 20% to 40% by weight, or even from 25% to 35% by weight, relative to the total weight of the composition.

Preferably, the total amount of acyl isethionate surfactant(s), and in particular those of formula (A) above, present in the composition of the invention is at least 10% by weight relative to the weight of the composition; it preferably ranges from 10% to 70% by weight, better still from 12% to 50% by weight, even better still from 15% to 45% by weight, preferentially from 20% to 40% by weight, or even from 25% to 35% by weight, relative to the total weight of the composition.

(ii) Esters of Fatty Acid(s)

The composition according to the invention also comprises (ii) one or more esters of fatty acid(s) comprising at least 12 carbon atoms. This is intended to mean that the acid, or at least one of the acids, serving to form the ester comprises at least 12 carbon atoms.

The esters of fatty acid(s) according to the invention can be liquid or solid at ambient temperature and at atmospheric pressure (25° C., 1 atm). Preferably, the esters of fatty acid(s) used are solid at ambient temperature and at atmospheric pressure (25° C., 1 atm).

Preferably, the esters of fatty acid(s) according to the invention are chosen from:
  (mono)esters of linear or branched, saturated carboxylic acids comprising at least 12 carbon atoms, and of linear or branched, saturated fatty monoalcohols comprising at least 10 carbon atoms. The saturated carboxylic acids preferably comprise from 12 to 30, or even from 14 to 28, carbon atoms and more particularly from 16 to 24 carbon atoms. They may optionally be hydroxylated. The saturated fatty monoalcohols preferably comprise from 10 to 30 carbon atoms and more particularly from 12 to 24 carbon atoms.
  (di)esters of linear or branched, saturated carboxylic acids comprising at least 12 carbon atoms, and of linear or branched diols comprising at least 2 carbon atoms. The saturated carboxylic acids preferably comprise from 12 to 30, or even from 14 to 28, carbon atoms and more particularly from 16 to 24 carbon atoms. They may optionally be hydroxylated. The diols preferably comprise from 2 to 8 carbon atoms and more particularly from 2 to 4 carbon atoms.

Preferably, the composition comprises at least one diester of linear saturated carboxylic acids comprising from 12 to 30, or even from 14 to 28, carbon atoms and more particularly from 16 to 24 carbon atoms, and of linear or branched diols comprising at least 2 carbon atoms.

Preferentially, the composition comprises at least one diester of linear saturated carboxylic acids comprising from 12 to 30, or even from 14 to 28, carbon atoms and more particularly from 16 to 24 carbon atoms, and of glycol (1,2-ethanediol); and more preferentially a glycol distearate.

The composition according to the invention can comprise said ester(s) of fatty acid(s) in an amount ranging from 0.1% to 15% by weight, in particular from 1% to 10% by weight and preferentially from 5% to 8% by weight, relative to the total weight of the composition.

In particular, the composition comprises glycol distearate in a content ranging from 0.1% to 15% by weight, in particular from 1% to 10% by weight and preferentially from 5% to 8% by weight, relative to the total weight of the composition.

(iii) Fatty Alcohol

The composition according to the invention also comprises (iii) one or more fatty alcohols comprising at least 16 carbon atoms.

The fatty alcohols according to the invention can be liquid or solid at ambient temperature and at atmospheric pressure (25° C., 1 atm). Preferably, the fatty alcohols used are solid at ambient temperature and at atmospheric pressure (25° C., 1 atm).

Preferably, the fatty alcohols according to the invention have the structure R—OH with R denoting a linear or branched, saturated or unsaturated hydrocarbon-based group optionally substituted with one or more hydroxyl groups, comprising from 16 to 30, better still from 16 to 24, or even from 16 to 20 and even better still from 16 to 18 carbon atoms. These fatty alcohols are neither oxyalkylenated nor glycerolated.

Preferably, R is a linear or branched, preferably linear, (saturated) alkyl group comprising from 16 to 20 carbon atoms, The fatty alcohols that can be used can be chosen, alone as a mixture, from cetyl alcohol (1-hexadecanol), stearyl alcohol (1-octadecanol), arachidyl alcohol (1-eicosanol), behenyl alcohol (1-docosanol), lignoceryl alcohol (1-tetracosanol), ceryl alcohol (1-hexacosanol), montanyl alcohol (1-octacosanol) and myricyl alcohol (1-triacontanol).

Preferentially, the composition comprises at least one fatty alcohol chosen from cetyl alcohol, stearyl alcohol, behenyl alcohol and mixtures thereof such as cetylstearyl alcohol or cetearyl alcohol.

The composition according to the invention can comprise said fatty alcohol(s) in an amount ranging from 0.1% to 15% by weight, in particular from 1% to 10% by weight and preferentially from 5% to 8% by weight, relative to the total weight of the composition.

In one preferred embodiment, the weight ratio, in the composition, between the esters of fatty acid(s) comprising at least 12 carbon atoms (ii) and the fatty alcohols comprising at least 16 carbon atoms (iii) is advantageously between 0.5 and 5, in particular between 0.7 and 3, or even between 0.8 and 2.5, even better still between 0.8 and 1.5, and most particularly is equal to 1.

In another preferred embodiment, the weight ratio, in the composition, between the glycol distearate and the fatty alcohols chosen from cetyl alcohol, stearyl alcohol, behenyl alcohol and mixtures thereof is advantageously between 0.5 and 5, in particular between 0.7 and 3, or even between 0.8 and 2.5, even better still between 0.8 and 1.5, and most particularly is equal to 1.

Polyols

The composition according to the invention may also comprise one or more polyols. Preferably, the polyol(s) of the invention is (are) not polysaccharides.

The polyols that may be used in the context of the present invention preferably have the formula:

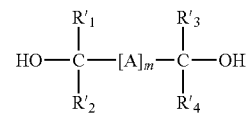

in which:
R'$_1$, R'$_2$, R'$_3$ and R'$_4$ denote, independently of each other, a hydrogen atom, a $C_1$-$C_6$ alkyl radical or a $C_1$-$C_6$ mono- or polyhydroxyalkyl radical, A denotes a linear or branched alkylene radical comprising from 1 to 18 carbon atoms, and optionally from 1 to 9 oxygen atoms, but no hydroxyl group, m denotes 0 or 1.

A first group of preferred polyols is constituted of the polyols having the formula above for which m=0.

Preferably, when m=0, R'1=R'2=R'3=H and R'4 is a $C_1$-$C_6$ polyhydroxyalkyl radical, preferably of —(CHOH)x- type with x=1 to 4.

Mention may in particular be made of 1,2,3-propanetriol (glycerol), propylene glycol (or 1,2-propanediol), pinacol (2,3-dimethyl-2,3-butanediol), 1,2,3-butanetriol, 2,3-butanediol, 1,2-octanediol and sorbitol.

A second group of preferred polyols is constituted of the polyols having the formula above for which m=1 and R'$_1$, R'$_2$, R'$_3$ and R'$_4$ denote, independently of one another, a hydrogen atom or a $C_1$-$C_6$ alkyl radical, such as polyethylene glycols, in particular those having from 4 to 9 ethylene oxide groups, for instance the products called PEG-6 or PEG-8 (CTFA name).

A third group of preferred polyols is constituted of the polyols having the formula above for which m=1 and R'$_1$, R'$_2$, R'$_3$ and R'$_4$ denote, independently of one another, a hydrogen atom, a $C_1$-$C_6$ alkyl radical or a $C_1$-$C_6$ mono- or polyhydroxyalkyl radical, and A denotes a linear or branched alkylene radical comprising 1 to 6 carbon atoms, such as 3-methyl-1,3,5-pentanetriol, 1,2,4-butanetriol, 1,5-pentanediol, 2-methyl-1,3-propanediol, 1,3-butanediol, 3-methyl-1,5-pentanediol, neopentyl glycol (2,2-dimethyl-1,3-propanediol), isoprene glycol (3-methyl-1,3-butanediol) and hexylene glycol (2-methyl-2,4-pentanediol), and even more preferably hexylene glycol, propylene glycol, neopentyl glycol and 3-methyl-1,5-pentanediol.

Preferably, the polymers used are liquid at 25° C., 1 atm.

Preferably, the composition according to the invention comprises one or more polyols more particularly chosen from glycerol, propylene glycol, sorbitol, polyethylene glycols, hexylene glycol, and mixtures thereof.

In one embodiment of the invention, and in particular when the weight ratio between the esters of fatty acid(s) comprising at least 12 carbon atoms (ii) and the fatty alcohols comprising at least 16 carbon atoms (iii) is greater than or equal to 1.5, in particular between 1.5 and 5, or even between 1.8 and 3, the composition according to the invention can advantageously comprise at least one polyol having the formula above, preferably in which m=0, R'1=R'2=R'3=H and R'4 is a $C_1$-$C_6$ polyhydroxyalkyl radical, preferably of —(CHOH)x- type with x=1 to 4; and most particularly sorbitol.

When the composition according to the invention comprises one or more polyols, the polyols are preferably present in the composition in a total amount ranging from 0.1% to 60% by weight, preferentially from 0.5% to 50% by weight, even better still from 1% to 30% by weight, or even from 5% to 25% by weight, relative to the total weight of the composition.

Cationic or Amphoteric Polymers

Advantageously, the composition according to the invention can also comprise one or more cationic or amphoteric polymers, which are non-silicone (that is to say do not comprise a silicone atom).

The term "cationic polymer" is intended to mean any polymer comprising cationic groups and/or groups that can be ionized to cationic groups.

Among the cationic polymers, mention may be made more particularly of:

(1) homopolymers or copolymers derived from acrylic or methacrylic esters or amides and comprising at least one of the units of the following formulae:

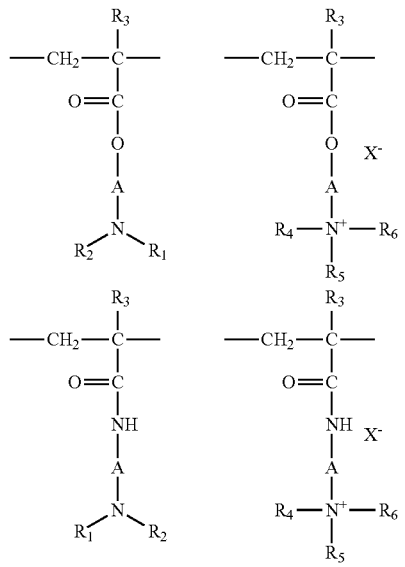

in which:
- $R_3$, which may be identical or different, denote a hydrogen atom or a $CH_3$ radical;
- A, which may be identical or different, represent a linear or branched divalent alkyl group of 1 to 6 carbon atoms, preferably 2 or 3 carbon atoms, or a hydroxyalkyl group of 1 to 4 carbon atoms;
- $R_4$, $R_5$ and $R_6$, which may be identical or different, represent an alkyl group containing from 1 to 18 carbon atoms or a benzyl radical, preferably an alkyl group containing from 1 to 6 carbon atoms;
- $R_1$ and $R_2$, which may be identical or different, represent a hydrogen atom or an alkyl group containing from 1 to 6 carbon atoms, preferably methyl or ethyl;
- X denotes an anion derived from a mineral or organic acid, such as a methosulfate anion or a halide such as chloride or bromide.

The copolymers of family (1) may also contain one or more units derived from comonomers that may be chosen from the family of acrylamides, methacrylamides, diacetone acrylamides, acrylamides and methacrylamides substituted on the nitrogen with lower ($C_1$-$C_4$) alkyls, acrylic or methacrylic acids or esters thereof, vinyllactams such as vinylpyrrolidone or vinylcaprolactam, and vinyl esters.

Among these copolymers of family (1), mention may be made of:
- copolymers of acrylamide and of dimethylaminoethyl methacrylate quaternized with dimethyl sulfate or with a dimethyl halide, such as that sold under the name Hercofloc by the company Hercules,
- copolymers of acrylamide and of methacryloyloxyethyltrimethylammonium chloride, such as the products sold under the name Bina Quat P 100 by the company Ciba Geigy,
- the copolymer of acrylamide and of methacryloyloxyethyltrimethylammonium methosulfate, such as that sold under the name Reten by the company Hercules,
- quaternized or non-quaternized vinylpyrrolidone/dialkylaminoalkyl acrylate or methacrylate copolymers, such as the products sold under the name Gafquat by the company ISP, for instance Gafquat 734 or Gafquat 755, or alternatively the products known as Copolymer 845, 958 and 937. These polymers are described in detail in French patents 2 077 143 and 2 393 573;
- dimethylaminoethyl methacrylate/vinylcaprolactam/vinylpyrrolidone terpolymers, such as the product sold under the name Gaffix VC 713 by the company ISP,
- vinylpyrrolidone/methacrylamidopropyldimethylamine copolymers, such as the copolymers sold under the name Styleze CC 10 by ISP;
- quaternized vinylpyrrolidone/dimethylaminopropylmethacrylamide copolymers such as the product sold under the name Gafquat HS 100 by the company ISP,
- preferably crosslinked polymers of methacryloyloxy($C_1$-$C_4$)alkyltri($C_1$-$C_4$)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homopolymerization or copolymerization being followed by crosslinking with an olefinically unsaturated compound, in particular methylenebisacrylamide. Use may be made more particularly of a crosslinked acrylamide/methacryloyloxyethyltrimethylammonium chloride copolymer (20/80 by weight) in the form of a dispersion comprising 50% by weight of said copolymer in mineral oil. This dispersion is sold under the name Salcare® SC 92 by the company Ciba. Use may also be made of a crosslinked methacryloyloxyethyltrimethylammonium chloride homopolymer comprising approximately 50% by weight of the homopolymer in mineral oil or in a liquid ester. These dispersions are sold under the names Salcare® SC 95 and Salcare® SC 96 by the company Ciba.

(2) cationic polysaccharides, in particular cationic celluloses and galactomannan gums. Among the cationic polysaccharides, mention may be made more particularly of cellulose ether derivatives comprising quaternary ammonium groups, cationic cellulose copolymers or cellulose derivatives grafted with a water-soluble quaternary ammonium monomer and cationic galactomannan gums.

The cellulose ether derivatives comprising quaternary ammonium groups are in particular described in FR 1 492 597, and mention may be made of the polymers sold under the name Ucare Polymer JR (JR 400 LT, JR 125 and JR 30M) or LR (LR 400 and LR 30M) by the company Amerchol. These polymers are also defined in the CTFA dictionary as quaternary ammoniums of hydroxyethylcellulose that have reacted with an epoxide substituted with a trimethylammonium group.

Cationic cellulose copolymers or cellulose derivatives grafted with a water-soluble quaternary ammonium monomer are described in particular in U.S. Pat. No. 4,131,576, and mention may be made of hydroxyalkyl celluloses, for instance hydroxymethyl-, hydroxyethyl- or hydroxypropylcelluloses grafted, in particular, with a methacryloylethyltrimethylammonium, methacrylamidopropyltrimethylammonium or dimethyldiallylammonium salt. The commercial products corresponding to this definition are more particularly the products sold under the names Celquat L 200 and Celquat H 100 by the company National Starch.

The cationic galactomannan gums are described more particularly in U.S. Pat. Nos. 3,589,578 and 4,031,307, and mention may be made of guar gums comprising cationic trialkylammonium groups. Use is made, for example, of guar gums modified with a 2,3-epoxypropyltrimethylammonium salt (for example, a chloride). Such products are in particular sold under the names Jaguar C13 S, Jaguar C 15, Jaguar C 17 and Jaguar C162 by the company Rhodia.

(3) polymers constituted piperazinyl units and divalent alkylene or hydroxyalkylene radicals containing linear or branched chains, optionally interrupted with oxygen, sulfur or nitrogen atoms or with aromatic or heterocyclic rings, and also the oxidation and/or quaternization products of these polymers.

(4) water-soluble polyaminoamides prepared in particular by polycondensation of an acidic compound with a polyamine; these polyaminoamides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyaminoamide; these polyaminoamides can be alkylated or, if they comprise one or more tertiary amine functions, they can be quaternized.

(5) polyaminoamide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical comprises from 1 to 4 carbon atoms and preferably denotes methyl, ethyl or propyl. Among these derivatives, mention may be made more particularly of the adipic acid/dimethylaminohydroxypropyl/diethylenetriamine polymers sold under the name Cartaretine F, F4 or F8 by the company Sandoz.

(6) polymers obtained by reacting a polyalkylene polyamine comprising two primary amine groups and at least one secondary amine group with a dicarboxylic acid chosen from diglycolic acid and saturated aliphatic dicarboxylic acids containing from 3 to 8 carbon atoms; the mole ratio between the polyalkylene polyamine and the dicarboxylic acid preferably being between 0.8:1 and 1.4:1; the resulting polyaminoamide being reacted with epichlorohydrin in a mole ratio of epichlorohydrin relative to the secondary amine group of the polyaminoamide preferably of between 0.5:1 and 1.8:1. Polymers of this type are sold in particular under the name Hercosett 57 by the company Hercules Inc. or else under the name PD 170 or Delsette 101 by the company Hercules in the case of the adipic acid/epoxypropyl/diethylenetriamine copolymer.

(7) cyclopolymers of alkyldiallylamine or of dialkyldiallylammonium, such as the homopolymers or copolymers containing, as main constituent of the chain, units corresponding to formula (I) or (II):

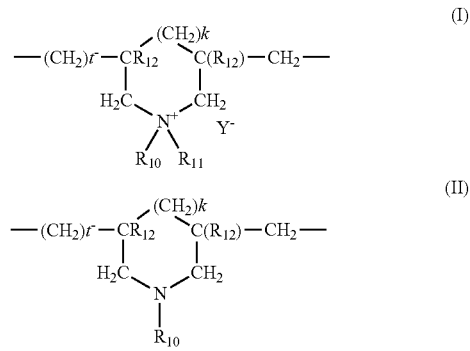

in which
k and t are equal to 0 or 1, the sum k+t being equal to 1;
$R_{12}$ denotes a hydrogen atom or a methyl radical;
$R_{10}$ and $R_{11}$, independently of each other, denote a $C_1$-$C_6$ alkyl group, a $C_1$-$C_5$ hydroxyalkyl group, a $C_1$-$C_4$ amidoalkyl group; or alternatively $R_{10}$ and $R_{11}$ may denote, together with the nitrogen atom to which they are attached, a heterocyclic group such as piperidyl or morpholinyl; $R_{10}$ and $R_{11}$, independently of each other, preferably denote a $C_1$-$C_4$ alkyl group;
$Y^-$ is an anion such as bromide, chloride, acetate, borate, citrate, tartrate, bisulfate, bisulfite, sulfate or phosphate.

Mention may be made more particularly of the homopolymer of dimethyldiallylammonium salts (for example chloride) for example sold under the name Merquat 100 by the company Nalco and the copolymers of diallyldimethylammonium salts (for example chloride) and of acrylamide, sold in particular under the name Merquat 550 or Merquat 7SPR.

(8) quaternary diammonium polymers comprising repeating units of formula:

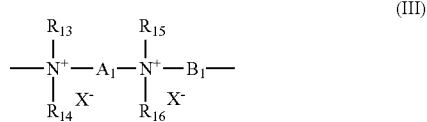

in which:
$R_{13}$, $R_{14}$, $R_{15}$ and $R_{16}$, which may be identical or different, represent aliphatic, alicyclic or arylaliphatic radicals comprising from 1 to 20 carbon atoms or $C_1$-$C_{12}$ hydroxyalkyl aliphatic radicals,
or else $R_{13}$, $R_{14}$, $R_{15}$ and $R_{16}$, together or separately, form, with the nitrogen atoms to which they are attached, heterocycles optionally comprising a second non-nitrogen heteroatom;
or else $R_{13}$, $R_{14}$, $R_{15}$ and $R_{16}$ represent a linear or branched $C_1$-$C_6$ alkyl radical substituted with a nitrile, ester, acyl, amide or —CO—O—$R_{17}$-D or —CO—NH—$R_{17}$-D group, where $R_{17}$ is an alkylene and D is a quaternary ammonium group;
$A_1$ and $B_1$ represent linear or branched, saturated or unsaturated, divalent polymethylene groups comprising from 2 to 20 carbon atoms, which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and $X^-$ denotes an anion derived from a mineral or organic acid;

it being understood that $A_1$, $R_{13}$ and $R_{15}$ can form, with the two nitrogen atoms to which they are attached, a piperazine ring;

in addition, if $A_1$ denotes a linear or branched, saturated or unsaturated alkylene or hydroxyalkylene radical, $B_1$ may also denote a group $(CH_2)n$-CO-D-OC—$(CH_2)p$- with n and p, which may be identical or different, being integers ranging from 2 to 20, and D denoting:
 a) a glycol residue of formula —O—Z—O—, in which Z denotes a linear or branched hydrocarbon-based radical, or a group corresponding to one of the following formulae: —$(CH_2CH_2O)x$-$CH_2CH_2$— and —[$CH_2CH(CH_3)O$]y-$CH_2CH(CH_3)$—, in which x and y denote an integer from 1 to 4, representing a defined and unique degree of polymerization or any number from 1 to 4 representing an average degree of polymerization;
 b) a bis-secondary diamine residue, such as a piperazine derivative;
 c) a bis-primary diamine residue of formula —NH—Y—NH—, in which Y denotes a linear or branched hydrocarbon-based radical, or else the divalent radical —$CH_2$—$CH_2$—S—S—$CH_2$—$CH_2$—;
 d) a ureylene group of formula —NH—CO—NH—.

Preferably, $X^-$ is an anion, such as chloride or bromide. These polymers have a number-average molar mass (Mn) generally of between 1000 and 100 000.

Mention may be made more particularly of polymers that are constituted of repeating units corresponding to the formula:

$$-\underset{\underset{R_2}{|}}{\overset{\overset{R_1}{|}}{N^+}}-(CH_2)_n-\underset{\underset{R_4}{|}}{\overset{\overset{R_3}{|}}{N^+}}-(CH_2)_p- \quad X^- \quad X^- \tag{IV}$$

in which $R_1$, $R_2$, $R_3$ and $R_4$, which may be identical or different, denote an alkyl or hydroxyalkyl radical containing from 1 to 4 carbon atoms, n and p are integers ranging from 2 to 20, and $X^-$ is an anion derived from a mineral or organic acid.

A particularly preferred compound of formula (IV) is the one for which $R_1$, $R_2$, $R_3$ and $R_4$ represent a methyl radical and n=3, p=6 and X=Cl, known as Hexadimethrine chloride according to the INCI (CTFA) nomenclature.

(9) polyquaternary ammonium polymers comprising units of formula (V):

$$-\underset{\underset{R_{19}}{|}}{\overset{\overset{R_{18}}{|}}{N^+}}-(CH_2)_r-NH-CO-(CH_2)_q-CO-NH-(CH_2)_s-\underset{\underset{R_{21}}{|}}{\overset{\overset{R_{20}}{|}}{N^+}}-A- \quad X^- \quad X^- \tag{V}$$

in which:
 $R_{18}$, $R_{19}$, $R_{20}$ and $R_{21}$, which may be identical or different, represent a hydrogen atom or a methyl, ethyl, propyl, β-hydroxyethyl, β-hydroxypropyl or —$CH_2CH_2$($OCH_2CH_2$)pOH radical, in which p is equal to 0 or to an integer between 1 and 6, with the proviso that $R_{18}$, $R_{19}$, $R_{20}$ and $R_{21}$ do not simultaneously represent a hydrogen atom,
 r and s, which may be identical or different, are integers between 1 and 6,
 q is equal to 0 or to an integer between 1 and 34,
 $X^-$ denotes an anion such as a halide,
 A denotes a divalent dihalide radical or preferably represents —$CH_2$—$CH_2$—O—$CH_2$—$CH_2$—.

Examples that may be mentioned include the products Mirapol® A 15, Mirapol® AD1, Mirapol® AZ1 and Mirapol® 175 sold by the company Miranol.

(10) quaternary polymers of vinylpyrrolidone and of vinylimidazole, for instance the products sold under the names Luviquat® FC 905, FC 550 and FC 370 by the company BASF.

(11) polyamines such as Polyquart® H sold by Cognis, referred to under the name Polyethylene glycol (15) tallow polyamine in the CTFA dictionary.

(12) polymers comprising in their structure:
(a) one or more units corresponding to formula (A) below:

$$-CH_2-\underset{\underset{NH_2}{|}}{CH}- \tag{A}$$

(b) optionally one or more units corresponding to formula (B) below:

$$-CH_2-\underset{\underset{\underset{O}{\overset{\|}{C}}-H}{\overset{|}{NH}}}{CH}- \tag{B}$$

In other words, these polymers may be chosen in particular from homopolymers or copolymers comprising one or more units derived from vinylamine and optionally one or more units derived from vinylformamide.

Preferably, these cationic polymers are chosen from polymers comprising, in their structure, from 5 mol % to 100 mol % of units corresponding to the formula (A) and from 0 to 95 mol % of units corresponding to the formula (B), preferably from 10 mol % to 100 mol % of units corresponding to the formula (A) and from 0 to 90 mol % of units corresponding to the formula (B).

These polymers may be obtained, for example, by partial hydrolysis of polyvinylformamide. This hydrolysis may take place in acidic or basic medium.

The weight-average molecular weight of said polymer, measured by light scattering, may range from 1000 to 3 000 000 g/mol, preferably from 10 000 to 1 000 000 and more particularly from 100 000 to 500 000 g/mol.

The polymers comprising units of formula (A) and optionally units of formula (B) are sold in particular under the Lupamin name by the company BASF, for instance, in a non-limiting way, the products provided under the names Lupamin 9095, Lupamin 5095, Lupamin 1095, Lupamin 9030 (or Luviquat 9030) and Lupamin 9010.

Other cationic polymers that may be used in the context of the invention are cationic proteins or cationic protein hydrolysates, polyalkyleneimines, in particular polyethyleneimines, polymers comprising vinylpyridine or vinylpyridinium units, condensates of polyamines and of epichlorohydrin, quaternary polyureylenes and chitin derivatives.

Preferably, the cationic polymers are chosen from those of families (1), (2), (7) and (10) mentioned above.

Preferentially, the cationic polymers are chosen from cationic polysaccharides, in particular cationic celluloses and cationic galactomannan gums, and in particular quaternary cellulose ether derivatives such as the products sold under the name JR 400 by the company Amerchol, cationic cyclopolymers, in particular dimethyldiallylammonium salt (for example chloride) homopolymers or copolymers, sold under the names Merquat 100, Merquat 550 and Merquat S by the company Nalco, quaternary polymers of vinylpyrrolidone and of vinylimidazole, optionally crosslinked homopolymers or copolymers of methacryloyloxy($C_1$-$C_4$)alkyltri($C_1$-$C_4$)alkylammonium salts, and mixtures thereof.

The composition can also comprise one or more amphoteric polymers, which can preferably be chosen from amphoteric polymers comprising the repetition of:
(i) one or more units derived from a (meth)acrylamide-type monomer,
(ii) one or more units derived from a (meth)acrylamidoalkyltrialkylammonium-type monomer, and
(iii) one or more units derived from a (meth)acrylic acid-type acid monomer.

Preferably, the units derived from a (meth)acrylamide-type monomer are units of structure (Ia) below:

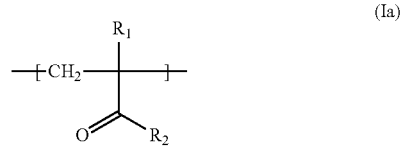

in which $R_1$ denotes H or $CH_3$ and $R_2$ is chosen from an amino, dimethylamino, tertbutylamino, dodecylamino and —NH—$CH_2$OH radical.

Preferably, said amphoteric polymer comprises the repetition of only one unit of formula (Ia).

The unit derived from a monomer of (meth)acrylamide type of formula (Ia) in which $R_1$ denotes H and $R_2$ is an amino radical ($NH_2$) is particularly preferred. It corresponds to the acrylamide monomer per se.

Preferably, the units derived from a monomer of (meth)acrylamidoalkyltrialkylammonium type are units of structure (IIa) below:

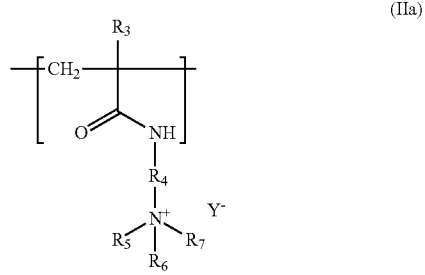

in which:
$R_3$ denotes H or $CH_3$,
$R_4$ denotes a group $(CH_2)k$, with k being an integer ranging from 1 to 6 and preferably from 2 to 4;
$R_5$, $R_6$ and $R_7$, which may be identical or different, denote a $C_1$-$C_4$ alkyl,
$Y^-$ is an anion such as bromide, chloride, acetate, borate, citrate, tartrate, bisulfate, bisulfite, sulfate or phosphate.

Preferably, said amphoteric polymer comprises the repetition of only one unit of formula (IIa).

Among these units derived from a (meth)acrylamidoalkyltrialkylammonium-type monomer of formula (IIa), the ones that are preferred are those derived from the methacrylamidopropyltrimethylammonium chloride monomer, for which $R_3$ denotes a methyl radical, k is equal to 3, $R_5$, $R_6$ and $R_7$ denote a methyl radical, and $Y^-$ denotes a chloride anion.

Preferably, the units derived from a monomer of (meth)acrylic acid type are units of formula (IIIa):

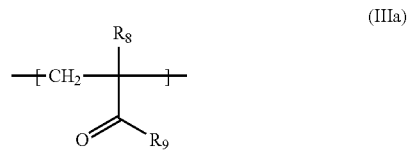

in which $R_8$ denotes H or $CH_3$ and $R_9$ denotes a hydroxyl radical or an —NH—$C(CH_3)_2$—$CH_2$—$SO_3$H radical.

The preferred units of formula (IIIa) correspond to the acrylic acid, methacrylic acid and 2-acrylamido-2-methylpropanesulfonic acid monomers.

Preferably, the unit derived from a monomer of (meth)acrylic acid type of formula (IIIa) is that derived from acrylic acid, for which $R_8$ denotes a hydrogen atom and $R_9$ denotes a hydroxyl radical.

The acidic monomer(s) of (meth)acrylic acid type may be non-neutralized or partially or totally neutralized with an organic or mineral base.

Preferably, said amphoteric polymer comprises the repetition of only one unit of formula (IIIa).

According to a preferred embodiment of the invention, the amphoteric polymer(s) of this type comprise at least 30 mol % of units derived from a monomer of (meth)acrylamide type (i). Preferably, they comprise from 30 mol % to 70 mol % and more preferably from 40 mol % to 60 mol % of units derived from a (meth)acrylamide-type monomer.

The content of units derived from a monomer of (meth)acrylamidoalkyltrialkylammonium type (ii) may advantageously be from 10 mol % to 60 mol % and preferentially from 20 mol % to 55 mol %.

The content of units derived from a monomer of (meth)acrylic acid type acidic (iii) may advantageously be from 1 mol % to 20 mol % and preferentially from 5 mol % to 15 mol %.

According to a particularly preferred embodiment of the invention, the amphoteric polymer of this type comprises:
from 30 mol % to 70 mol % and more preferably from 40 mol % to 60 mol % of units derived from a monomer of (meth)acrylamide type (i),
from 10 mol % to 60 mol % and preferentially from 20 mol % to 55 mol % of units derived from a monomer of (meth)acrylamidoalkyltrialkylammonium type (ii), and
from 1 mol % to 20 mol % and preferentially from 5 mol % to 15 mol % of units derived from a monomer of (meth)acrylic acid type (iii).

Amphoteric polymers of this type may also comprise additional units, other than the units derived from a (meth)acrylamide-type monomer, a (meth)acrylamidoalkyltrialkylammonium-type monomer and a (meth)acrylic acid-type monomer as described above.

However, according to a preferred embodiment of the invention, said amphoteric polymers are constituted solely of units derived from monomers of (meth)acrylamide type (i), of (meth)acrylamidoalkyltrialkylammonium type (ii) and of (meth)acrylic acid type (iii).

Mention may be made, as an example of particularly preferred amphoteric polymers, of acrylamide/methacrylamidopropyltrimethylammonium chloride/acrylic acid terpolymers. Such polymers are listed in the CTFA dictionary (INCI) under the name "Polyquaternium 53". Corresponding products are in particular sold under the names Merquat 2003 and Merquat 2003 PR by Nalco.

As another type of amphoteric polymer that may be used, mention may also be made of copolymers based on (meth) acrylic acid and on a dialkyldiallylammonium salt, such as copolymers of (meth)acrylic acid and of dimethyldiallylammonium chloride. An example that may be mentioned is Merquat 280 sold by Nalco.

The composition according to the invention may comprise the cationic and/or amphoteric polymers in an amount of between 0.01% and 5% by weight, in particular from 0.05% to 3% by weight and preferentially from 0.1% to 2% by weight, relative to the total weight of the composition.

Silicones

Advantageously, the composition according to the invention may also comprise one or more silicones.

The silicones that may be used can be chosen from polydialkylsiloxanes, in particular polydimethylsiloxanes (PDMSs), and organomodified polysiloxanes comprising at least one functional group preferably chosen from aryl groups, amino groups, alkoxy groups and polyoxyethylenated or polyoxypropylenated groups.

The silicones may be volatile or non-volatile, and may be in the form of an oil, a gum or a resin; silicone oils and gums are preferred.

When they are volatile, the silicones may be more particularly chosen from those with a boiling point of between 60° C. and 260° C., and even more particularly from:

(i) cyclic polydialkylsiloxanes containing from 3 to 7 and preferably from 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof. Mention may also be made of cyclocopolymers of the dimethylsiloxane/methylalkylsiloxane type, such as Silicone Volatile® FZ 3109 sold by Union Carbide, of formula:

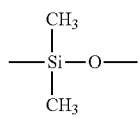

with D":

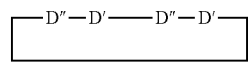

with D':

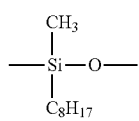

Mention may also be made of mixtures of cyclic polydialkylsiloxanes with organosilicon compounds, such as the mixture of octamethylcyclotetrasiloxane and tetra(trimethylsilyl)pentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers "Volatile Silicone Fluids for Cosmetics".

Use is preferably made of non-volatile polydialkylsiloxanes, polyorganosiloxanes modified with the organofunctional groups above, and mixtures thereof. These silicones are more particularly chosen from polydialkylsiloxanes, among which mention may be made mainly of polydimethylsiloxanes bearing trimethylsilyl end groups. The viscosity of the silicones is measured at 25° C. according to ASTM Standard 445 Appendix C.

Among these polydialkylsiloxanes, mention may be made of the following commercial products:

- the Silbione® oils of the 47 and 70 047 series or the Mirasil® oils sold by Rhodia, such as, for example, the oil 70 047 V 500 000;
- the oils of the Mirasil® series sold by the company Rhodia;
- the oils of the 200 series from the company Dow Corning, such as DC200 with a viscosity of 60 000 mm$^2$/s;
- the Viscasil® oils from General Electric and certain oils of the SF series (SF 96, SF 18) from General Electric.

Mention may also be made of polydimethylsiloxanes bearing dimethylsilanol end groups, known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are poly($C_1$-$C_{20}$)dialkylsiloxanes.

Products that may be used more particularly in accordance with the invention are mixtures such as:

- the mixtures formed from a polydimethylsiloxane hydroxylated at the chain end, or dimethiconol (CTFA), and from a cyclic polydimethylsiloxane, also known as cyclomethicone (CTFA), such as the product Q2-1401 sold by the company Dow Corning.

The organomodified silicones that may be used in the present invention are in particular silicones as defined above and comprising in their structure one or more organofunctional groups attached via a hydrocarbon-based group.

The organomodified silicones may be polydiarylsiloxanes, in particular polydiphenylsiloxanes, and polyalkylarylsiloxanes, functionalized with the organofunctional groups mentioned previously.

The polyalkylarylsiloxanes are particularly chosen from linear and/or branched polydimethyl/methylphenylsiloxanes and polydimethyl/diphenylsiloxanes with a viscosity ranging from $1 \times 10^{-5}$ to $5 \times 10^{-2}$ m$^2$/s at 25° C.

Among these polyalkylarylsiloxanes, mention may be made of the products sold under the following names:

- the Silbione® oils of the 70 641 series from Rhodia;
- the oils of the Rhodorsil® 70 633 and 763 series from Rhodia;
- the oil Dow Corning 556 Cosmetic Grade Fluid from Dow Corning;

the silicones of the PK series from Bayer, such as the product PK20;

the silicones of the PN and PH series from Bayer, such as the products PN1000 and PH1000;

certain oils of the SF series from General Electric, such as SF 1023, SF 1154, SF 1250 and SF 1265.

Among the organomodified silicones, mention may also be made of polyorganosiloxanes comprising:

substituted or unsubstituted amine groups, for instance the products sold under the names GP 4 Silicone Fluid and GP 7100 by the company Genesee. The substituted amine groups are in particular $C_1$-$C_4$ aminoalkyl groups;

alkoxy groups such as the product sold under the name Silicone Copolymer F-755 by SWS Silicones;

oxyethylenated or oxypropylenated groups.

In one variant of the invention, the silicones are not organomodified.

Preferably, the silicones are cationic or non-ionic.

The silicones used may also be chosen from amino silicones, and in particular may correspond to the formula below:

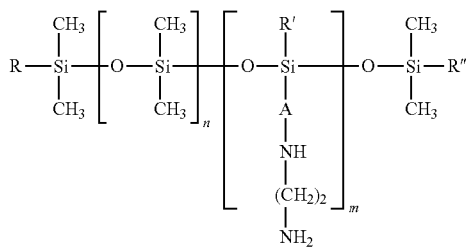

in which R, R' and R", which may be identical or different, denote a $C_1$-$C_4$ alkyl radical, preferably $CH_3$; a $C_1$-$C_4$ alkoxy radical, preferably methoxy; or OH; A represents a linear or branched, $C_1$-$C_8$ and preferably $C_3$-$C_6$ alkylene radical; m and n are integers dependent on the molecular weight and the sum of which is between 1 and 2000.

According to a first possibility, R, R' and R", which may be identical or different, represent a $C_1$-$C_4$ alkyl, preferably methyl, radical or a hydroxyl radical, A represents a $C_1$-$C_8$, preferably $C_3$-$C_4$, alkylene radical, and m and n are such that the weight-average molecular weight of the compound is between 5000 and 500 000 approximately. The compounds of this type are named "amodimethicone" in the CTFA dictionary.

According to a second possibility, R, R' and R", which may be identical or different, represent a $C_1$-$C_4$ alkoxy or hydroxyl radical, at least one of the R or R" radicals is an alkoxy radical and A represents a $C_3$ alkylene radical. The hydroxyl/alkoxy mole ratio is preferably between 0.2/1 and 0.4/1 and advantageously equal to 0.3/1. Moreover, m and n are such that the weight-average molecular weight of the compound is between 2000 and $10^6$. More particularly, n is between 0 and 999 and m is between 1 and 1000, the sum of n and m being between 1 and 1000. In this category of compounds, mention may be made, inter alia, of the product Belsil® ADM 652 sold by Wacker.

According to a third possibility, R and R", which may be different, represent a $C_1$-$C_4$ alkoxy or hydroxyl radical, at least one of the R and R" radicals is an alkoxy radical, R' represents a methyl radical and A represents a $C_3$ alkylene radical. The hydroxyl/alkoxy mole ratio is preferably between 1/0.8 and 1/1.1 and advantageously is equal to 1/0.95. Moreover, m and n are such that the weight-average molecular weight of the compound is between 2000 and 200 000. More particularly, n is between 0 and 999 and m is between 1 and 1000, the sum of n and m being between 1 and 1000. More particularly, mention may be made of the product Fluid WR® 1300 sold by Wacker.

Preferably, the amino silicone has a weight-average molecular weight ranging from 75 000 to 1 000 000 and preferentially ranging from 100 000 to 200 000. The weight-average molecular weights of these amino silicones are measured by gel permeation chromatography (GPC) at ambient temperature, as polystyrene equivalents. The columns used are µ styragel columns. The eluent is THF and the flow rate is 1 ml/min. 200 µl of a 0.5% by weight solution of silicone in THF are injected. Detection is performed by refractometry and UV-metry.

The composition according to the invention can comprise the silicone(s) in an amount ranging from 0.01% to 15% by weight, in particular from 0.1% to 10% by weight and preferentially from 1% to 5% by weight, relative to the total weight of the composition.

Solid Particles

The composition according to the invention may also comprise at least one type of solid particles; it may quite obviously comprise several different types of solid particles. These solid particles are different from the fatty alcohols and from the esters of fatty acid(s) previously described.

Said solid particles are generally water-insoluble.

For the purposes of the present invention, the term "water-insoluble compound" is intended to mean a compound of which the solubility in water at 25° C. and at atmospheric pressure is less than 0.1% and better still less than 0.001%.

Advantageously, said particles have a number-average primary size ranging from 0.001 to 1000 µm, preferably from 0.01 to 700 µm, preferentially from 0.5 to 200 µm. For the purposes of the present invention, the term "primary particle size" is intended to mean the maximum dimension that it is possible to measure between two diametrically opposite points of an individual particle. The size of the particles may be determined by transmission electron microscopy or by measuring the specific surface area via the BET method or by laser particle size analysis.

The composition according to the invention preferably comprises particles of one or more mineral compounds (or mineral particles), in particular chosen from oxides, inorganic salts, carbides, nitrides, borides, sulfides and hydroxides.

Mention may in particular be made of clays, silicates, alumina, silica, kaolin and hydroxyapatite.

The clay particles are products that are already well known per se, which are described, for example, in the publication Minéralogie des argiles [Mineralogy of Clays], S. Caillère, S. Hénin, M. Rautureau, 2nd Edition 1982, Masson.

Clays are silicates containing a cation that may be chosen from calcium, magnesium, aluminium, sodium, potassium and lithium cations, and mixtures thereof.

Mention may in particular be made of clays of the smectite family such as montmorillonites, hectorites, bentonites, beidellites and saponites, and also of the vermiculite, stevensite or chlorite family.

The clays may be of natural or synthetic origin. Preferably, clays that are cosmetically compatible and acceptable with keratin fibres such as the hair are used.

The clay may be chosen from montmorillonite, bentonite, hectorite, attapulgite and sepiolite, and mixtures thereof. Preferably, the clay is a bentonite or a hectorite. The clays may be chosen from organophilic clays. Organophilic clays are clays modified with a chemical compound chosen from quaternary amines, tertiary amines, amine acetates, imidazolines, amine soaps, fatty sulfates, alkyl aryl sulfonates and amine oxides, and mixtures thereof. Preferably, the organophilic clays according to the invention are clays modified with a chemical compound chosen from quaternary amines. Organophilic clays that may be mentioned include quaternium-18 bentonites such as those sold under the names Bentone 3, Bentone 38 and Bentone 38V by the company Elementis, Tixogel VP by the company United Catalyst, and Claytone 34, Claytone 40 and Claytone XL by the company Southern Clay; stearalkonium bentonites such as those sold under the names Bentone 27V by the company Elementis, Tixogel LG by the company United Catalyst, and Claytone AF and Claytone APA by the company Southern Clay; quaternium-18/benzalkonium bentonites such as those sold under the names Claytone HT and Claytone PS by the company Southern Clay. The organophilic clay is in particular chosen from modified hectorites such as hectorite modified with $C_{10}$-$C_{12}$ fatty acid ammonium chloride, in particular distearyldimethylammonium chloride and stearylbenzyldimethylammonium chloride.

Among the silicates, mention may also be made of magnesium silicates (or talc).

Preferably, the particles of one or more mineral compounds are chosen from calcium carbonate, silica and talc.

When the composition according to the invention comprises one or more solid particles, the solid particles are preferably present in the composition in an amount ranging from 0.001% to 15% by weight, preferentially from 0.1% to 10% by weight, even better still from 0.5% to 80% by weight, relative to the total weight of the composition.

Additional Ingredients

The composition according to the invention may also comprise other ingredients commonly used in cosmetic compositions. Such ingredients may be chosen from nonionic, amphoteric or cationic surfactants; antioxidants, fragrances, essential oils, preservatives, cosmetic active agents, moisturizers, vitamins, sunscreens, emulsifiers, thickeners, gelling agents, spreading agents, wetting agents, dispersants, antifoams, neutralizing agents, stabilizers, and mixtures thereof. Needless to say, those skilled in the art will take care to select these optional additional ingredients, and/or the amount thereof, such that the advantageous properties of the composition according to the invention are not, or are not substantially, adversely affected by the envisioned addition.

The composition according to the invention may be anhydrous or aqueous. Preferably, the composition according to the invention is aqueous. It can preferably comprise at least 5% by weight of water, in particular from 5% to 80% by weight of water, in particular from 10% to 70% by weight, or even from 15% to 60% by weight, better still from 20% to 50% by weight, even better still from 20% to 45% by weight, relative to the total weight of the composition.

The composition may also additionally comprise one or more organic solvents that are liquid at 25° C., 1 atm, other than the abovementioned compounds, such as $C_1$-$C_7$ alcohols, in particular aliphatic or aromatic $C_1$-$C_7$ monoalcohols, such as ethanol, isopropanol, benzyl alcohol and mixtures thereof.

Preferably, the composition has a pH of between 3 and 9, in particular between 4 and 7, preferentially between 4.5 and 6.5, even better still between 5 and 6.

The compositions according to the invention can be prepared by mixing the various ingredients while hot, at a temperature of between 30 and 80° C., for example by mixing an aqueous phase and a fatty phase, in particular in the case of the presence of solid fatty substances.

The cosmetic composition according to the invention in particular finds a particularly advantageous application in the field of hair hygiene, in particular for caring for, cleaning and/or conditioning keratin materials, in particular cleaning the hair.

The hair compositions are preferably shampoos, or compositions for preventing hair loss, or which are antidandruff or antiseborrhoeic.

The cosmetic composition may optionally be rinsed off after having been applied to the keratin materials. It can thus optionally be rinsed off, for example with water, after an optional leave-on time. The composition is preferably rinsed off.

A subject of the invention is also a cosmetic treatment method, in particular for caring for, cleaning and/or conditioning keratin materials, in particular the hair, which consists in applying a composition as described above to said keratin materials, and in optionally rinsing, for example with water, after an optional leave-on time. Preferably, rinsing is carried out after an optional leave-on time.

It is preferably a hair treatment method, for cleaning or washing the hair.

The present invention is illustrated in greater detail in the examples that follow (% AM=% of active material in the composition).

EXAMPLE A: COMPOSITIONS A-C (COMPARATIVE) AND 1-4 (INVENTION)

Washing hair compositions comprising the following ingredients (% by weight of active material=AM) are prepared:

| | Example A comparative | Example B comparative | Example C comparative | Example 1 |
|---|---|---|---|---|
| Sodium cocoyl isethionate (HOSTAPON SCI 85) | 29% AM | 29% AM | 29% AM | 29% AM |
| Caprylyl glycol | 0.2 | 0.2 | 0.2 | 0.2 |
| Glycerol | 15 | 30 | 15 | 15 |
| Dimethiconol | 3% AM | 3% AM | 3% AM | 3% AM |
| Polyquaternium-6 | 0.72% AM | 0.72% AM | 0.72% AM | 0.72% AM |
| Talc | 2 | 2 | 2 | 2 |
| Glycol distearate | 6.7 | — | 6.7 | 6.7 |
| Cetearyl alcohol | — | 6.7 | — | 6.7 |
| Myristyl alcohol | — | — | 6.7 | — |
| Fragrance, preservative | qs | qs | qs | qs |
| pH agent | qs pH 5.5 | qs pH 5.5 | qs pH 5.5 | qs pH 5.5 |
| Water | qs 100% | qs 100% | qs 100% | qs 100% |
| Fatty acid ester/fatty alcohol ratio | — | — | — | 1 |

|  | Example 2 | Example 3 | Example 4 |
|---|---|---|---|
| Sodium cocoyl isethionate (HOSTAPON SCI 85) | 29% AM | 29% AM | 29% AM |
| Caprylyl glycol | 0.2 | 0.2 | 0.2 |
| Glycerol | 15 | — | 15 |
| Dimethiconol | 3% AM | 3% AM | 3% AM |
| Polyquaternium-6 | 0.72% AM | 0.72% AM | 0.72% AM |
| Hydrogenated starch hydrolysate | — | 21% AM | — |
| Talc | 2 | 2 | 2 |
| Glycol distearate | 6.7 | 6.7 | 6.7 |
| Cetearyl alcohol | — | 3.4 | — |
| Stearyl alcohol | — | — | 6.7 |
| Cetyl alcohol | 6.7 | — | — |
| Myristyl alcohol | — | — | — |
| Fragrance, preservative | qs | qs | qs |
| pH agent | qs pH 5.5 | qs pH 5.5 | qs pH 5.5 |
| Water | qs 100% | qs 100% | qs 100% |
| Fatty acid ester/fatty alcohol ratio | 1 | 1.97 | 1 |

The compositions according to the examples are in the form of flexible solids for the purposes of the invention.

These compositions can be used for cleaning the hair. During use, good distribution of the product on the head of hair, and also the obtaining of a creamy, smooth and abundant foam, are observed. The compositions rinse off and are eliminated easily. Furthermore, they confer very good cosmetic properties on the hair, in particular easy untangling and softness.

EXAMPLE B: STABILITY MEASUREMENT

The hardness of some of the compositions prepared above was evaluated over time, during their storage at ambient temperature (25° C.) or at 45° C.

The hardness is represented by the penetration force determined by penetrometry, with a tip having a diameter of 1.5 cm and at a speed of 10 mm/s. The texture analysis measurements are carried out at 25° C. using a Stable Micro Systems TA.XT Plus texture analyser. The penetrometry experiments are carried out with a metal rod which has a Delrin screw tip, 15 mm in diameter and 6 mm high, connected to the measuring head. The piston pushes into the sample at a constant speed of 10 mm/s, to a height of 15 mm or 20 mm depending on the height of product in the pot (of diameter 90 mm, and height 30 mm, made of plastic).

The force exerted on the piston is recorded and the average value of the force is calculated. The higher the penetration force, the harder the composition.

The following results are obtained:

| Example | T0 | T1 25° C. | T2 25° C. | T3 25° C. | T1 45° C. | T2 45° C. | T3 45° C. |
|---|---|---|---|---|---|---|---|
| A | 194 | 316 | 351 | 431 | 818 | 804 | 919 |
| B | 129 | 152 | 162 | 154 | 530 | 483 | 446 |
| C | 185 | 232 | 243 | 322 | 623 | 601 | 463 |
| 1 | 57 | 74 | 78 | 72 | 175 | 192 | 181 |
| 2 | 71 | 86 | 82 | 88 | 325 | 314 | 306 |
| 4 | 42 | 42 | 45 | 52 | 94 | 120 | 86 |

T0: hardness measured 24 h after production
T1: hardness measured after 1 week of storage (at 25° C. or at 45° C.)
T2: hardness measured after 1 month of storage
T3: hardness measured after 2 months of storage The compositions according to the invention 1, 2 and 4 exhibit small variations in the penetration force during the storage period, both at 25° C. and at 45° C., contrary to the comparative compositions A, B and C.

The invention claimed is:

1. An aqueous cosmetic composition in flexible solid form, comprising:
   (i) at least 10% by weight of one or more anionic surfactants comprising a sulfonate group,
   (ii) one or more esters of fatty acid(s) comprising at least 12 carbon atoms, and
   (iii) one or more fatty alcohols comprising at least 16 carbon atoms,
   wherein the weight ratio of the esters of fatty acid(s) to the fatty alcohols is between 0.5 and 5.

2. The composition according to claim 1, wherein the composition has a penetration force of greater than or equal to 40 g at 25° C.

3. The composition according to claim 1, wherein the composition has a penetration force ranging from 50 to 600 g at 25° C.

4. The composition according to claim 1, wherein the composition has a threshold stress of greater than or equal to 100 Pa at 25° C.

5. The composition according to claim 1, wherein the composition has a threshold stress ranging from 100 to 900 Pa at 25° C.

6. The composition according to claim 1, which has a viscoelastic spectrum between $10^{-2}$ Hz and 100 Hz at 25° C., such that there is no crossover point between curves G' and G", wherein G' is greater than G".

7. The composition according to claim 1, wherein the anionic surfactants comprising a sulfonate group are chosen, alone or as a mixture, from:
   $C_6$-$C_{24}$ alkylsulfosuccinates;
   $C_6$-$C_{24}$ alkyl ether sulfosuccinates;
   ($C_6$-$C_{24}$)acyl isethionates.

8. The composition according to claim 1, further comprising one or more additional anionic surfactants chosen, alone or as a mixture, from:
   $C_6$-$C_{24}$ alkyl sulfates or salts thereof;
   $C_6$-$C_{24}$ alkyl ether sulfates or salts thereof;
   $C_6$-$C_{24}$ acyl glutamates or salts thereof;
   $C_6$-$C_{24}$ acylsarcosinates or salts thereof.

9. The composition according to claim 1, wherein the total amount of anionic surfactant(s) comprising a sulfonate group is from 10% to 70% by weight, relative to the total weight of the composition.

10. The composition according to claim 1, wherein the esters of fatty acid(s) are chosen from:
   (mono)esters of linear or branched, saturated carboxylic acids comprising at least 12 carbon atoms and linear or branched, saturated fatty monoalcohols comprising at least 10 carbon atoms;

(di)esters of linear or branched, saturated carboxylic acids comprising at least 12 carbon atoms and linear or branched diols comprising at least 2 carbon atoms.

11. The composition according to claim 1, comprising said ester(s) of fatty acid(s) in an amount ranging from 0.1% to 15% by weight, relative to the total weight of the composition.

12. The composition according to claim 1, wherein the fatty alcohols have a linear or branched, saturated or unsaturated hydrocarbon group optionally substituted with one or more hydroxyl groups, comprising from 16 to 30 carbon atoms.

13. The composition according to claim 1, comprising said fatty alcohol(s) in an amount ranging from 0.1% to 15% by weight, relative to the total weight of the composition.

14. The composition according to claim 1, wherein the weight ratio between the esters of fatty acid(s) and the fatty alcohols is between 0.7 and 3.

15. The composition according to claim 1, further comprising one or more polyols having the formula:

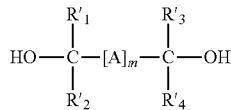

wherein:

$R'_1$, $R'_2$, $R'_3$, and $R'_4$ represent, independently of each other, a hydrogen atom, a $C_1$-$C_6$ alkyl radical or a $C_1$-$C_6$ mono- or polyhydroxyalkyl radical, A represents a linear or branched alkylene radical comprising from 1 to 18 carbon atoms, and optionally from 1 to 9 oxygen atoms, but no hydroxyl group, m represents 0 or 1.

16. The composition according to claim 15, wherein the polyols are present in a total amount ranging from 0.1% to 60% by weight, relative to the total weight of the composition.

17. The composition according to claim 1, further comprising one or more non-silicone cationic or amphoteric polymers.

18. The composition according to claim 1, further comprising one or more non-silicone cationic or amphoteric polymers in an amount of between 0.01% and 5% by weight, relative to the total weight of the composition.

19. The composition according to claim 1, comprising at least 5% by weight of water, relative to the total weight of the composition.

20. A cosmetic treatment method for caring for keratin materials, comprising applying an aqueous cosmetic composition in flexible solid form to said keratin materials, and optionally rinsing the composition, wherein the composition comprises:
(i) at least 10% by weight of one or more anionic surfactants comprising a sulfonate group,
(ii) one or more esters of fatty acid(s) comprising at least 12 carbon atoms, and
(iii) one or more fatty alcohols comprising at least 16 carbon atoms, wherein the weight ratio of the esters of fatty acid(s) and to the fatty alcohols is between 0.5 and 5.

* * * * *